United States Patent
Chen et al.

(10) Patent No.: US 6,794,886 B1
(45) Date of Patent: Sep. 21, 2004

(54) TANK PROBE FOR MEASURING SURFACE CONDUCTANCE

(75) Inventors: Dong Chen, Goleta, CA (US); John Alexander, Sunnyvale, CA (US); Amin Samsavar, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/202,980

(22) Filed: Jul. 24, 2002

Related U.S. Application Data (60) Provisional application No. 60/335,876, filed on Nov. 1, 2001.

(51) Int. Cl.[7] .............................................. G01R 27/08
(52) U.S. Cl. ........................ 324/716; 324/719; 324/693
(58) Field of Search ................................ 324/716, 719, 324/635, 644, 693, 724, 750, 765, 699, 754–762

(56) References Cited

U.S. PATENT DOCUMENTS

| | | | | |
|---|---|---|---|---|
| 4,839,112 A | * | 6/1989 | Wynne et al. | 264/435 |
| 5,483,172 A | * | 1/1996 | Radford | 324/693 |
| 5,508,610 A | * | 4/1996 | Feeney et al. | 324/233 |
| 5,528,142 A | * | 6/1996 | Feickert | 324/236 |
| 5,811,664 A | * | 9/1998 | Whittington et al. | 324/204 |
| 6,072,313 A | * | 6/2000 | Li et al. | 324/230 |
| 6,407,546 B1 | * | 6/2002 | Le et al. | 324/230 |
| 6,433,541 B1 | * | 8/2002 | Lehman et al. | 324/230 |
| 6,434,541 B1 | | 8/2002 | Tawel et al. | |
| 6,445,187 B1 | * | 9/2002 | Montgomery et al. | 324/346 |
| 6,448,795 B1 | * | 9/2002 | Ermakov et al. | 324/724 |
| 6,462,538 B2 | * | 10/2002 | Harada | 324/224 |
| 6,480,013 B1 | * | 11/2002 | Nayler et al. | 324/754 |

* cited by examiner

*Primary Examiner*—Timothy J. Dole
(74) *Attorney, Agent, or Firm*—Beyer Weaver & Thomas, LLP (57) ABSTRACT

A highly sensitive, non-contact tank probe to measure surface conductance of thin film structures, and a method for using the same, are described. The tank probe includes inductor (L), capacitor (C) and resistor (R) circuitry that is driven by a signal generator at the probe's resonant frequency. The conductance of a film structure specimen is determined from measuring the signal that is reflected from the tank probe and it respective frequency. Various types of information can be obtained from the tank probe. For instance, information as to film thickness, doping concentration, and the presence of defects can be obtained. In one embodiment of the invention, the tank probe is formed of integrated circuits within a semiconductor substrate. Another aspect of the present invention pertains to a method of using the tank probe system to measure the conductivity of a material specimen.

22 Claims, 7 Drawing Sheets

TANK PROBE FOR MEASURING SURFACE CONDUCTANCE

This application claims priority of U.S. Provisional Patent Application No. 60/335,876, filed Nov. 1, 2001 entitled "Tank Probe For Measuring Surface Conductance," which is hereby incorporated by reference.

FIELD OF THE INVENTION

The present invention relates generally to film thickness measurements, and more specifically to a film thickness measurement technique that measures surface conductance.

BACKGROUND OF THE INVENTION

The industry of semiconductor manufacturing involves highly complex techniques for integrating circuits into semiconductor materials. Due to the large scale of circuit integration and the decreasing size of semiconductor devices, the semiconductor manufacturing process is prone to processing defects. Testing procedures are therefore critical to maintain quality control. Since the testing procedures are an integral and significant part of the manufacturing process, the semiconductor industry constantly seeks more accurate and efficient testing procedures.

A critical aspect of semiconductor fabrication involves the formation of the multiple conductive layers and liner layers. Each conductive layer includes the metal traces, also referred to as interconnects, which form the paths along which electronic signals travel within semiconductor devices. Dielectric material layers and liner layers separate conductive layers. The dielectric material layer, commonly silicon dioxide, provides electrical insulation between the conductive layers. Portions of each conductive layer are connected to portions of other conductive layers by electrical pathways called "plugs." The liner layers are formed between each conductive layer and each dielectric material layer to prevent the conductive material from diffusing into the dielectric material layer. The liner layer inhibits a conductive layer from diffusing into an underlying dielectric and shorting circuiting with an adjacent 30 conductive layer. Of course, such short circuit formations are likely to be detrimental to semiconductor performance. In particular note, copper, a common conductive material used in semiconductor devices, diffuses very aggressively into silicon dioxide. The thickness and composition of the conductive and liner layers must be formed under extremely small margins of error. Thus, systems capable of testing the characteristics of these layers are very important.

Some of the current methods for measuring conductive film stack characteristics include eddy current testing, microwave probe testing, four-point probe testing, X-ray fluorescence testing, and photo-induced surface acoustic wave testing. Unfortunately, each of these methods has associated disadvantages that limit their usefulness. Specifically, the eddy current probes have difficulty resolving small variations in thin film thickness and also have spot sizes that are relatively large in comparison to areas of interest on a semiconductor device. Eddy current probes have low resolution for thin films for at least a couple of reasons. First, conventional eddy current probes use large inductor coils (in the mm range) that are driven at relatively low frequencies (kHz range). Such probe systems create electromagnetic fields that penetrate too deep to resolve the thickness of thin films. Secondly, film thickness measurements by eddy current probe systems are based upon impedance values of the probe. Unfortunately, the probe's impedance is not sufficiently sensitive to film thickness to provide high resolution of thin films.

Microwave probes are generally formed of a conductive core positioned within a cylindrical housing. The probe is driven at its resonant frequency such that a standing wave is created in the cylindrical housing and such the probe absorbs a maximum amount of energy from the signal generator. Measurements are made by placing the probe next to a specimen and measuring the change in the reflected signal and the resonant frequency shift. The reflected signal is the strength of a signal emitted from, or reflected out of, the probe due to the fact that the interaction between the specimen and the probe reduces the probe's ability to absorb energy from the signal generator. The interaction specifically involves the conductance of the specimen changing the inductance and resistance of the microwave probe. The resonant frequency shift is the shift in the reflected signal's frequency that occurs when the probe is placed next to the specimen. Even though microwave probes operate at high frequencies and therefore have high resolutions for particular thin films, the usefulness of these probes are limited because they are not sensitive to high conductance materials. This is particularly limiting considering the fact that copper has a high conductance value and is commonly used in thin film applications.

A disadvantage of the four-point probe test system is that it requires the destruction of specimens. Also, the distance between the four probes of the test system, which must make contact with the specimen, limits the lateral resolution of the test system. Similarly, X-ray fluorescence testing is also limited by large spot sizes. Additionally, X-ray fluorescence methods have difficulty distinguishing different film stacks thickness, generally results in poor measurements, and are time consuming processes. It is important for the testing speeds to keep pace with the increasing fabrication speeds so that the goals of maximizing manufacturing throughput may be achieved. A specific problem with photo-induced surface acoustic wave methods is that they have difficulty resolving the thickness of copper layers; copper being a common conductor used in semiconductors.

In light of the foregoing, a probe system capable of achieving high resolution for thin film thickness measurements, and achieving such high resolution for high conductance materials, would be desirable.

BRIEF SUMMARY OF THE INVENTION

The present invention allows for a non-contact, high frequency, and high-resolution schemes for thin metal film and surface conductance measurements. The present invention further allows for thickness measurements of high conductance materials. The conductance of a film structure specimen is determined from measuring the signal that is reflected from the probe and the frequency of the reflected signal.

One aspect of the present invention pertains to a tank probe system that includes a tank probe and a measurement instrument. The tank probe includes an inductor, a capacitor, and a resistor. The measurement instrument is connected to the tank probe by a transmission line. The measurement instrument includes a signal generator that sends a driving signal to the tank probe, and a signal analysis module configured to detect and measure a reflected signal from the tank probe and the frequency of the reflected signal, wherein the conductivity of the material specimen is determined from the reflected signal and the frequency of the reflected signal. In one embodiment of the invention, the tank probe is formed of integrated circuits within a semiconductor substrate. Another aspect of the present invention pertains to a method of using the tank probe system to measure the conductivity of a material specimen.

These and other features and advantages of the present invention will be presented in more detail in the following specification of the invention and the accompanying figures, which illustrate by way of example the principles of the invention.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE INVENTION

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known operations have not been described in detail so not to unnecessarily obscure the present invention.

The present invention is a highly sensitive, non-contact tank probe to measure surface conductance of thin film structures. The tank probe includes inductor (L), capacitor (C) and resistor (R) circuitry that is driven by a signal generator at the probe's resonant frequency. The conductance of a film structure specimen is determined from measuring the signal that is reflected from the tank probe and it respective frequency. High-resolution data results are possible because the reflected signal and its frequency are very sensitive to the physical and electromagnetic properties of the film structure specimen. Various types of information can be obtained from the tank probe. For instance, information as to film thickness, doping concentration, and the presence of defects can be obtained.

Figure 1:
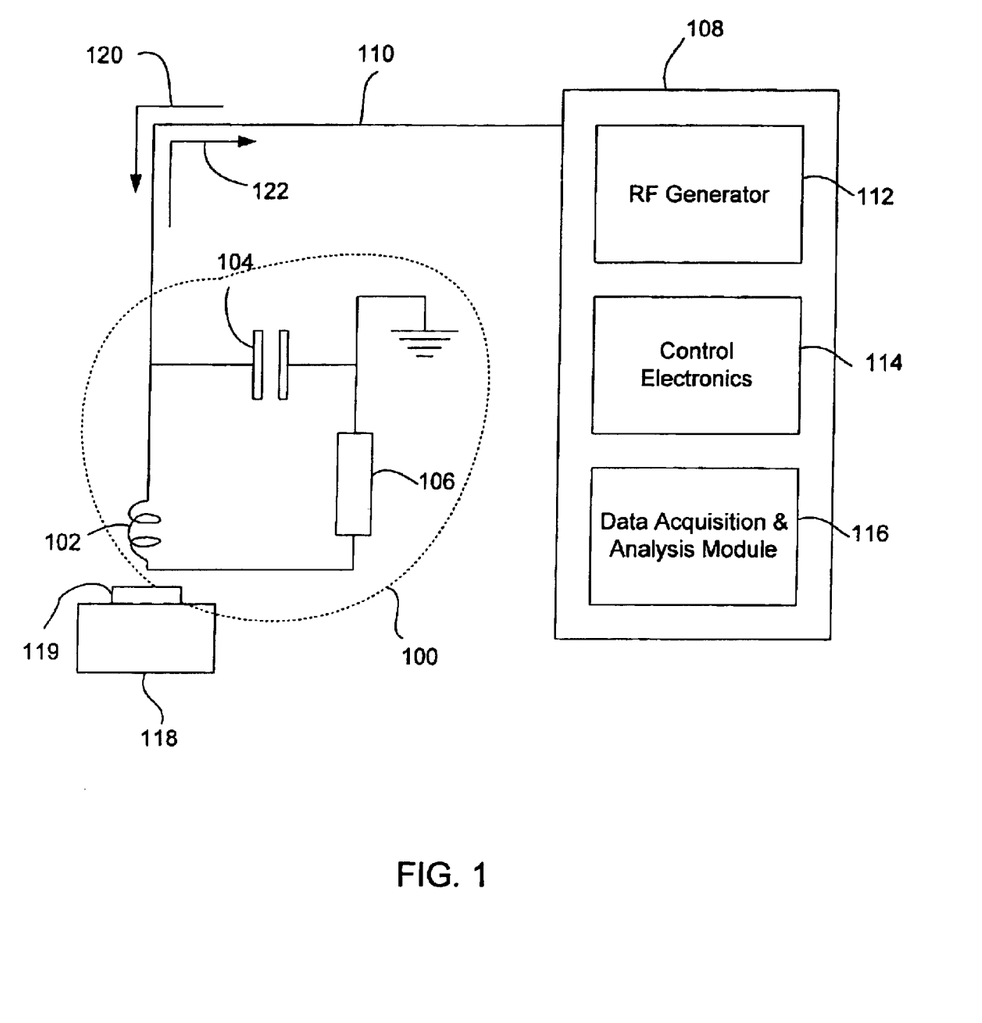
FIG. 1 is a diagrammatic representation of tank probe according to one embodiment of the present invention.

FIG. 1 is a diagrammatic representation of tank probe 100 according to one embodiment of the present invention. Tank probe 100 includes an inductor 102, a capacitor 104, and a resistor 106. The tank probe 100 is connected to a measurement instrument 108 via a transmission line 1 10. The transmission line is a cable such as a strip line wave guide or a coaxial cable. Measurement instrument 108 includes a RF generator 112, control electronics 114, and an analysis module 116. A sample stage 118 secures a specimen 1 19 near tank probe 100 during analysis. Sample stage 118 can be manually or automatically controlled using a micrometer to implement the probe sampling process.

The electronic circuitry of tank probe 100 forms an LCR resonator. During operation, RF signal generator 112 drives tank probe 100 at or near its resonant frequency such that tank probe 100, like a fuel tank, stores a maximum possible amount energy. Inductor 102 is very small coil, preferably being approximately equal to or less than 100 urn in diameter. In one embodiment, the coil has just one turn. In another embodiment, the measurement is performed in a scribe line of a patterned wafer. The measurement can be performed on a test structure. The diameter of the probe would be a fraction of the size of the test structure or the scribe line. This fraction can be one third of the size of the feature of the interest. This is to minimize any proximity effects from neighboring sites. Typically, the tank probe can obtain measurement resolutions that are approximately three times the size of the diameter of inductor 102. For example an inductor with diameter of 33 microns can obtain resolution of approximately 100 microns.

Tank probe 100 can be used to measure various material properties associated with the conductance of the material. One specific property is the thickness of a film structure, Tank probe 100 can be configured to measure the thickness of films in the range of zero to 2 microns. To measure such thin films, tank probe 100 is not designed to directly measure changes in impedance, inductance or resistance, according to known convention. Measuring such properties is difficult because the values change very little as a function of film thickness when the thickness is very small. Therefore, to obtain the thin film resolution desired, the present invention measures the signal that is reflected out of tank probe 100 when probe 100 is brought near a film specimen. Specifically, both the strength and frequency of the "reflected" signal are measured. The reflected signal is associated with the surface conduction of the film specimen, and therefore provides information as to the film structure. Directional arrows 120 and 122 represent the driving signal from signal generator 112 and the reflected signal, respectively.

Even through the tank probe 100 is generally intended to measure the thickness of thin films, tank probe 100 can also be configured to measure relatively thicker Cu films. For example the thickness of Cu films in the range of 1 to 10 um can also be measured.

The association between the reflected signal and the specimen's conductive property is described now. When the probe is brought near a sample film structure, the oscillating electromagnetic field of the tank probe induces an eddy current in the sample structure. This eddy current interacts with the tank probe such that the inductance and resistance of the tank probe changes. These changes either cause some of the energy stored within the resonating tank probe to reflect out because the tank probe is no longer able to store as much energy, or more energy is caused to be stored within tank probe such that a reflected signal becomes weaker. Tank probe 100 obtains high-resolution measurements of a sample structure's conductivity by detecting the strength and frequency of these reflected signals. After determining the conductivity from the reflected signal, various film structure properties can then also be determined. The thickness of a film structure can be measured when its surface conductivity is constant.

The tank probe achieves high-resolution measurements for thin films also because it operates at high frequencies, in ranges up to approximately 1 GHz. At such high frequencies, the tank probe has a skin depth (EM field penetration depth) of approximately 2.2 microns and has small proximity effects. The frequency at which the tank probe operates can be adjusted to control the skin depth. The ability to adjust the operational frequency is advantageous in that the frequency can be adjusted to optimize the tank probe's sensitivity. Specifically, the tank probe's sensitivity is optimized when the frequency is set such that the skin depth is about equal to the film thickness being measured. Therefore, the sensitivity of the tank probe can be tuned to measure the thickness of various film structures.

The ability to tune the tank probe allows the tank probe to be used in a variety of manners. For example, tuning the tank probe to the thickness of various film structures allows the tank probe to be used as a "go/no-go gauge," rather than an actual thickness measurement tool. That is, a tool designed to simply give either a positive or negative indication depending upon the thickness of a film. Also, the ability to adjust the frequency of the tank probe allows the tank probe to be used as a conductivity depth-probing tool.

The tank probe can also be tuned such that the reflected signal is minimized when the tank probe's impedance matches that of the signal generator and the transmission line. Such tuning allows for better signal-to-noise ratios when detecting the reflected signal and its respective frequency. To tune the tank probe, C, L and R can be adjusted. Preferably, C and L are adjusted, as opposed to adjusting R, with C being the easiest to adjust. For example, if the transmission line 110 has impedance of 50 Ohms, then L, C and R can be adjusted to have a matching 50 Ohms of impedance. When measuring film structure thickness, tank probe can have thickness sensitivity within 1%.

Figure 2:
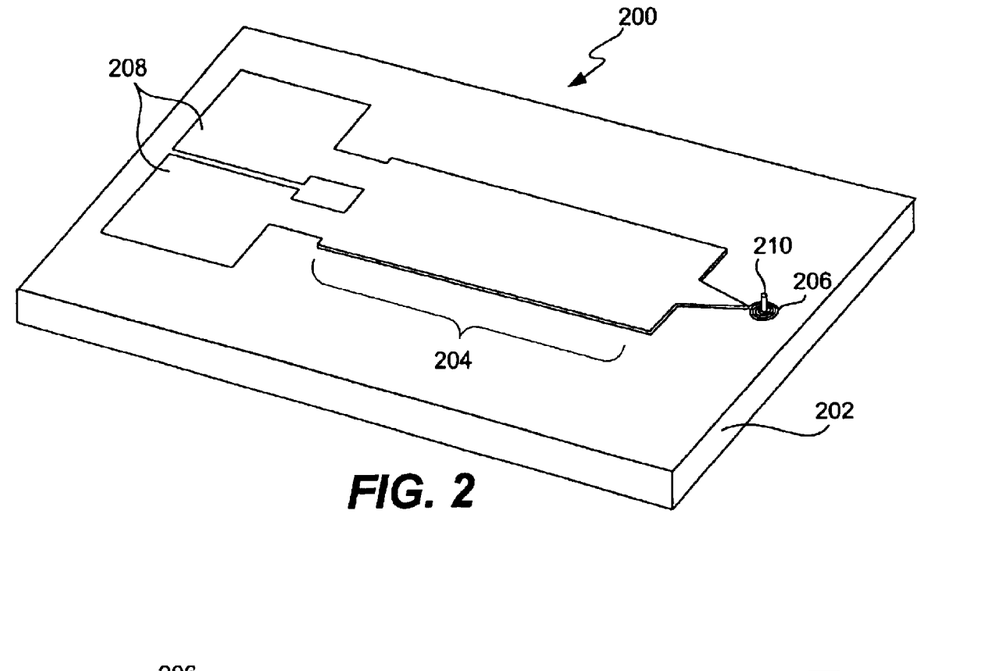
FIG. 2 illustrates a perspective view of an alternative embodiment of a tank probe wherein it is formed of circuits integrated within a semiconductor substrate.

FIG. 2 illustrates a perspective view of an alternative embodiment of a tank probe 200 wherein it is formed of circuits integrated within a semiconductor substrate 202. Tank probe 200, as in the embodiment of FIG. 1, includes a capacitor 204, an inductor 206, and a resistor. Contact pads 208 provide connection points to attach tank probe 200 to measurement instruments. Tank probe 200 is manufactured using techniques similar to those used for manufacturing semiconductor chips.

Discrete resistor circuitry can be integrated into tank probe 200 or the inherent resistance of inductor 206 can provide the resistance of the tank probe 200. The thickness of the trace forming inductor 206 affects the resistance value of tank probe 200. Aluminum can be used form inductor 206. Focusing element 210 tends to focus the direction of the electromagnetic field emitted from inductor 206. In the embodiment of FIG. 2, the electromagnetic field is directed along the longitudinal axis of focusing element 210, which is rod (or needle) shaped. Focusing element 210 is an optional component of tank probe 200. It is furthermore possible to focus the field by using counter-coils and their resultant evanescent fields as the electric field for probing a sample film structure. Such focusing techniques are known in the art of read-write heads for hard disks.

In an alternative embodiment of tank probe 200, inductor coil 206 is coated with an insulating material. This coating can be, for example, elastic, a polymer or Teflon. The coating allows the tank probe 200 circuitry to be placed in contact with a film structure being measured without damage to the specimen. A non-conductive coating having a controlled load force can set the gap repeatably to a desired position. In other words, the distance between tank probe 200 and the film structure can be maintained at a constant distance. During measurements involving contact, the test apparatus implementing the tank probe must be adjusted to apply a controlled load upon the tank probe such that no damage is done to the specimen.

Figure 3:
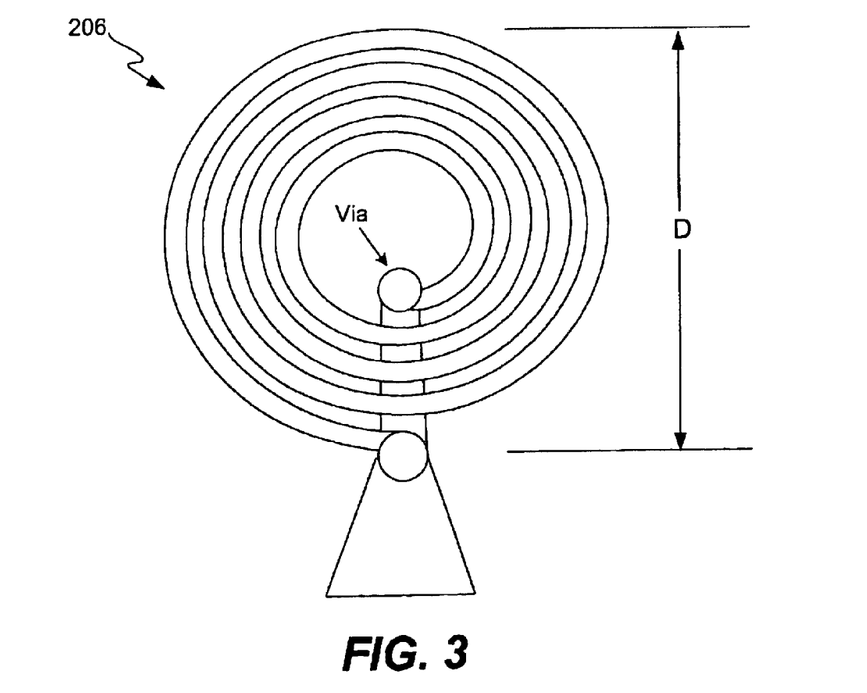
FIG. 3 illustrates an enlarged plan view of inductor coil of FIG. 2.

FIG. 3 illustrates an enlarged plan view of inductor coil 206 of FIG. 2. As mentioned above, coil 206 with diameter, D has a measurement resolution of approximately three times the size of For example, coil 206 having a diameter, D of about 33 microns can accurately measure a film structure that is about 100 microns thick. Such a coil 206 can have a trace thickness of approximately 1.5 microns. For high lateral resolution applications, it is preferable to use a micro-fabricated tank probe as shown in FIG. 2, which has high inductance and low resistance. High lateral resolution of approximately 50 um can be achieved by the tank probe. The magnetic field of the micro-coil 206 can be focused at its center by forming the coil 206 of ferrite materials.

Figure 4:
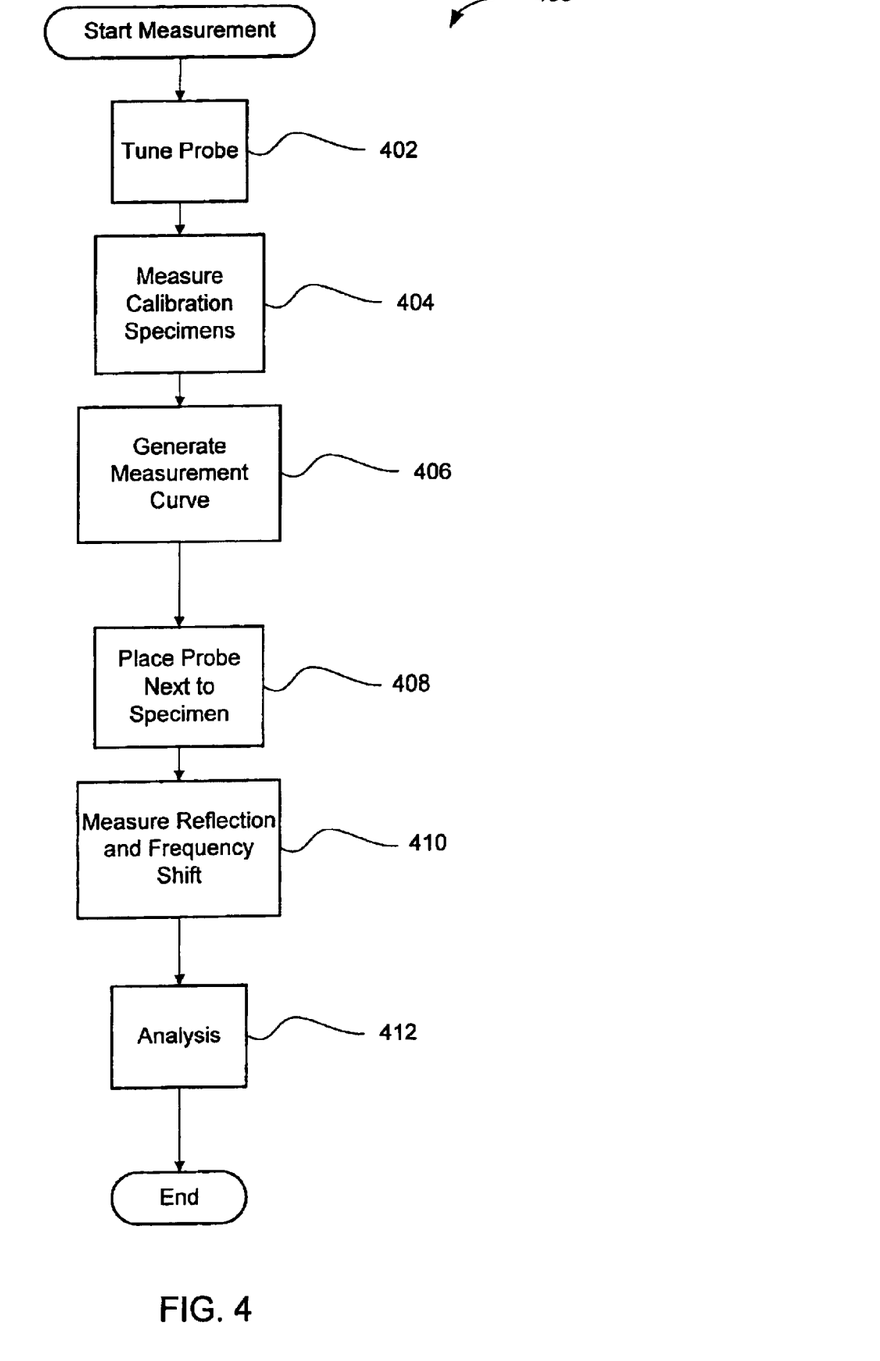
FIG. 4 illustrates a flow diagram that shows one implementation for using the tank probe of the present invention.

FIG. 4 illustrates a flow diagram 400 that shows one implementation for using the tank probe of the present invention. The process described in flow diagram 400 can be implemented to obtain various types of information that are associated to a film structure's conductivity, as mentioned above. The process begins at operation 402 by tuning the tank probe to reduce the noise associated with detecting changes in reflectance signals and frequencies. To begin with, the driving signal frequency is set to the resonant frequency of the tank probe. Tuning is performed by setting the L and C values such that the tank probe's impedance matches that of the transmission line. It is noted that tuning can also be performed just before actually placing the probe next to a sample film structure.

In operation 404, the tank probe is calibrated by placing the tank probe next to various film structure specimens with known physical properties of the type that the tank probe will be used to measure. For example, a tank probe to be used to measure film thickness will be calibrated against sample film structures with known thickness values. The calibration operation determines the relationship between reflected signal readings and film structure specimen properties. Note that the frequency of this calibration step can be controlled. It may not be required to perform this calibration prior to each measurement, especially if a particular probe has been previously calibrated.

Figure 5:
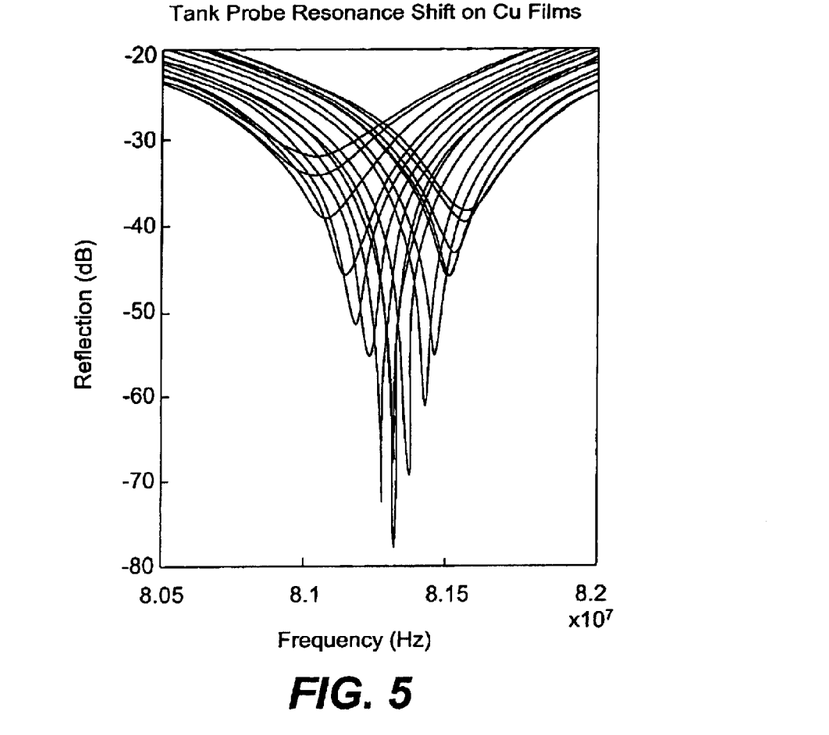
FIGS. 5 and 6 illustrate graphs of reflected signal values versus the frequency of the reflected signal.
Figure 6:
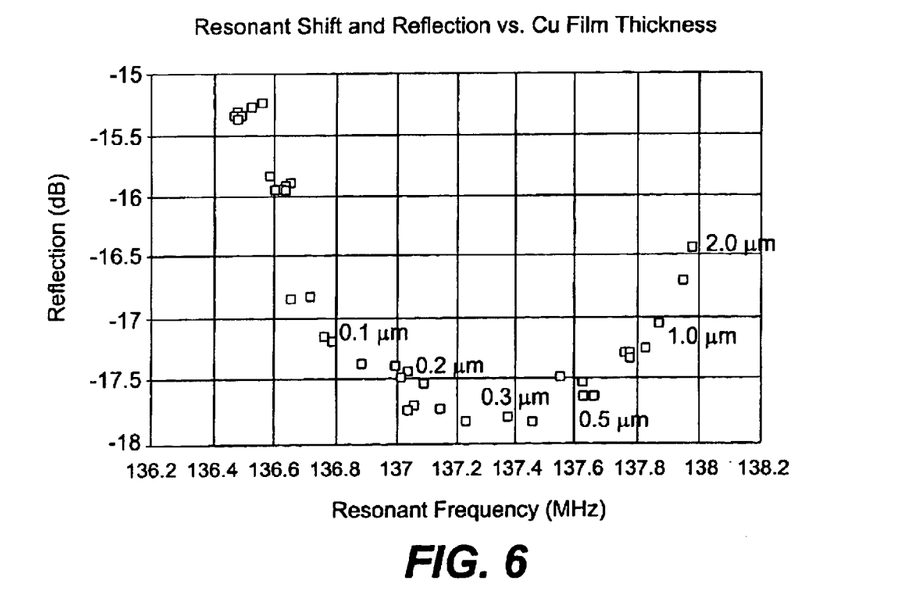

In operation 406, calibration measurement curves are generated. FIGS. 5 and 6 illustrate such calibration measurement curves. Specifically, FIGS. 5 and 6 illustrate graphs of reflected signal values versus the frequency of the reflected signal. FIG. 6 more clearly plots points with respect to the thickness of various film structures. Both FIGS. 5 and 6 show how the reflected signal value and its frequency shifts with respect to various film structures, wherein each film structure has a different thickness. The calibration operations provide the information in FIGS. 5 and 6, which therefore allows film structure properties (e.g., thickness) to be determined. Specifically, the change in the reflected signal strength and the reflected signal frequency provides the required test data.

In operation 408, a test operator places the tank probe next to a film structure to be tested. In certain test procedures, the distance separating the tank probe and the film structure must be precisely regulated. Typically, the distance separating the tank probe and the film structure should be minimized. This will be further discussed below.

In operation 410, measurement values of a reflected signal and its frequency are obtained. In operation 412, a test operator or the data analysis module 116 compares test results with the calibration values to determine film structure property values of interest. The operations of process 400 are preferably performed at constant temperature for accurate results. However, it is possible to use temperature dependence curves, which would allow test results to be adjusted to compensate for temperature effects.

Figure 7:
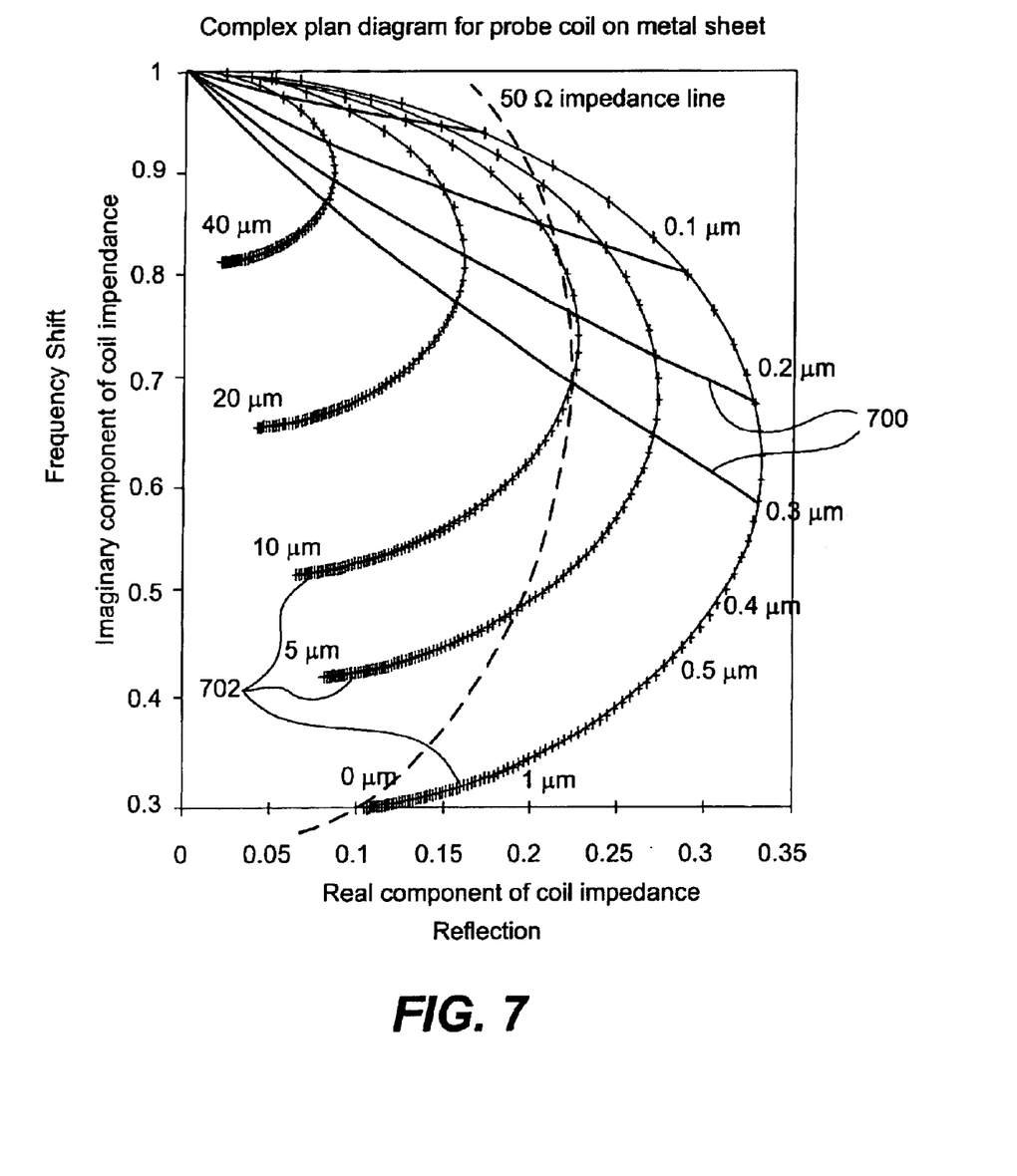
FIG. 7 illustrates a graph of lift curves against a coordinate system of reflection versus frequency shift, which can be used to determine the thickness of specimen film structures.

Techniques for using the tank probe, other than the technique described in the flow diagram of FIG. 4, can also be used to obtain useful information about a film structure. For example, FIG. 7 illustrates a graph of lift curves 700, against a coordinate system of reflection versus frequency shift, which can be used to determine the thickness of specimen film structures. The "life curve" technique is based on the proportionate reaction between the tank probe and a film specimen in relation to their separation distance. The "lift curve" technique has also been used with other probe systems such as eddy current probes.

To implement this technique, calibration steps of obtaining reference lift curves 700 is required. Calibration is performed using film structures having known thickness values. Each reference lift curve represents the relationship between a reflected signal and its frequency shift based upon the separation distance between the tank probe and the film structure. Arcing lines 702 represent the relationship between a reflected signal and its frequency at uniform distances.

With the reference lift curve information, the thickness of a film structure can be determined by first obtaining the reflectance and frequency values for that specimen. Then, the thickness of the film structure is determined by matching the test results to calibration information. Specifically, the test results are correlated to a reference lift curve corresponding to a specific film thickness. The thickness of the film structure can be determined without knowledge of the gap between the tank probe and the film structure. Actually, the gap distance can be determined from the test information.

The tank probe of the present invention can be used to measure film structure characteristics that are related to conductivity other than thickness. For example, tank probe can also be used to determine doping concentration and the presence of physical and electrical defects (such as voids). Doping concentration can be detected since the electrical conductivity of material is physically related to the amount of doping that a material has received. In a related manner, the tank probe can be scanned over a specimen to obtain a conductance map, which would indicate the conductivity in each specific area of a film structure.

The tank probe can also be used to detect physical and electrical defects because they also affect the conductivity of a material. For instance, voids in a film structure would cause the material's conductivity to decrease.

The tank probe can also be used for set point monitoring, which is the process of monitoring for aberrations of a specific property value outside of a standard deviation. For example, a deviation in a specific property value would be indicated by a change in the reflected signal The tank probe therefore provides a very sensitive set point monitoring system. A specific use of set point monitoring is the quality assurance that a film structure has uniform thickness or conductivity.

The tank probe of the present invention can be used apart from other devices, such as semiconductor fabrication devices. However, the tank probe is very useful as a high-throughput process-monitoring device used in combination with manufacturing devices. Such manufacturing devices can be, for example, a photolithography, metal deposition, or ion deposition device. The tank probe can be used in-situ or ex-situ with such devices. Tank probe system can also be used in tandem with other metrology tools such as X-ray diffraction tools and electron beams. The combination of the tank probe with such other metrology tools can yield enhanced measurement performance ranges. For example, a film thickness-monitoring tool such as Rudolph's MetaPulse can measure film thickness while the tank probe can measure film conductivity. In addition to being used with other devices, multiple tank probes can be implemented within a single system wherein each tank probe is configured to detect a particular specimen parameter.

The tank probe is made of simple electronic circuitry and is therefore cost effective, as well as able to take measurements quickly. The tank probe system of the present invention can perform its functions at a throughput rate of at least 50 semiconductor wafers per hour.

Figure 8:
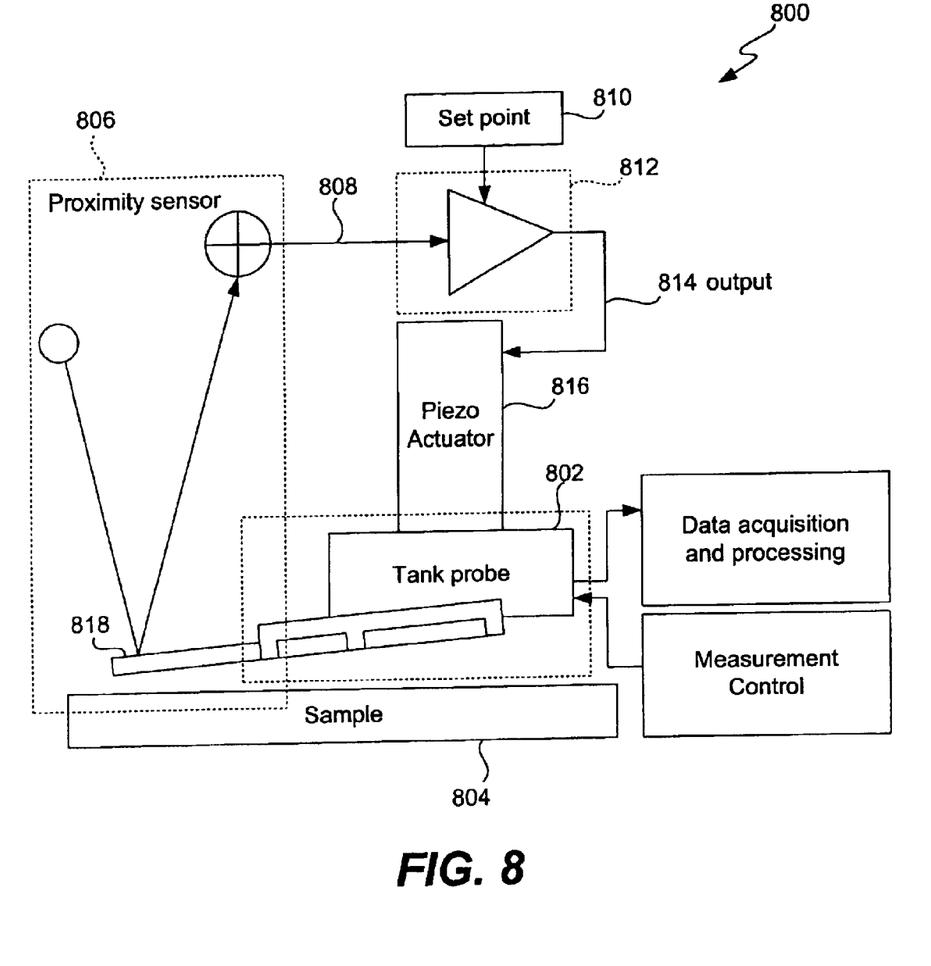
FIG. 8 illustrates a typical non-contact measurement test system that utilizes the tank probe.

FIG. 8 is now presented to show a typical non-contact measurement test system 800 that utilizes the tank probe. A feedback control loop of test system 800 allows the tank probe to be used in a non-contact manner by regulating the distance between the probe 802 and the sample 804. The distance between probe 802 and sample 804 is detected using a proximity sensor 806. The output signal 808 of proximity sensor 806 is compared with a set point signal 810 at integrator circuit 812. The output signal 814 of integrator circuit 812 is used to drive actuator 816, such as a piezo-actuator, which maintains a constant distance between tank probe 802 and sample 804. In the configuration of FIG. 8, proximity sensor 806 is a cantilever 818 that is driven near its resonant frequency. The amplitude of the cantilever 818 can be measured through various techniques that include optical sensors and interferometry. When cantilever 818 is brought into the proximity of the sample's 804 surface, its amplitude is damped by the interaction between cantilever and the sample 804. The average amplitude of the cantilever maintains probe 802 within a desired separation distance from sample 804. The cantilever-surface distance determines the degree of damping. Therefore, the distance between tank probe 802 and the sample 804 can be regulated by maintaining a constant cantilever amplitude. Preferably, the separation distance between the probe and the sample should be as small as possible. As mentioned earlier, the tank probe can also be used when the probe is placed in contact with the film structure.

In an alternative embodiment, the proximity sensor 806 uses air damping techniques, which are well known art in the scanning probe microscopy field. The air damping can change the resonance of the cantilever 818 in FIG. 8. It is furthermore possible to attach the tank probe to a tuning fork to regulate the gap between the probe and a specimen. The resonance of the tuning fork as it and a tank probe are brought to a close proximity with a specimen is effected. This can serve as an alternative method of regulating the measurement gap.

Figure 9:
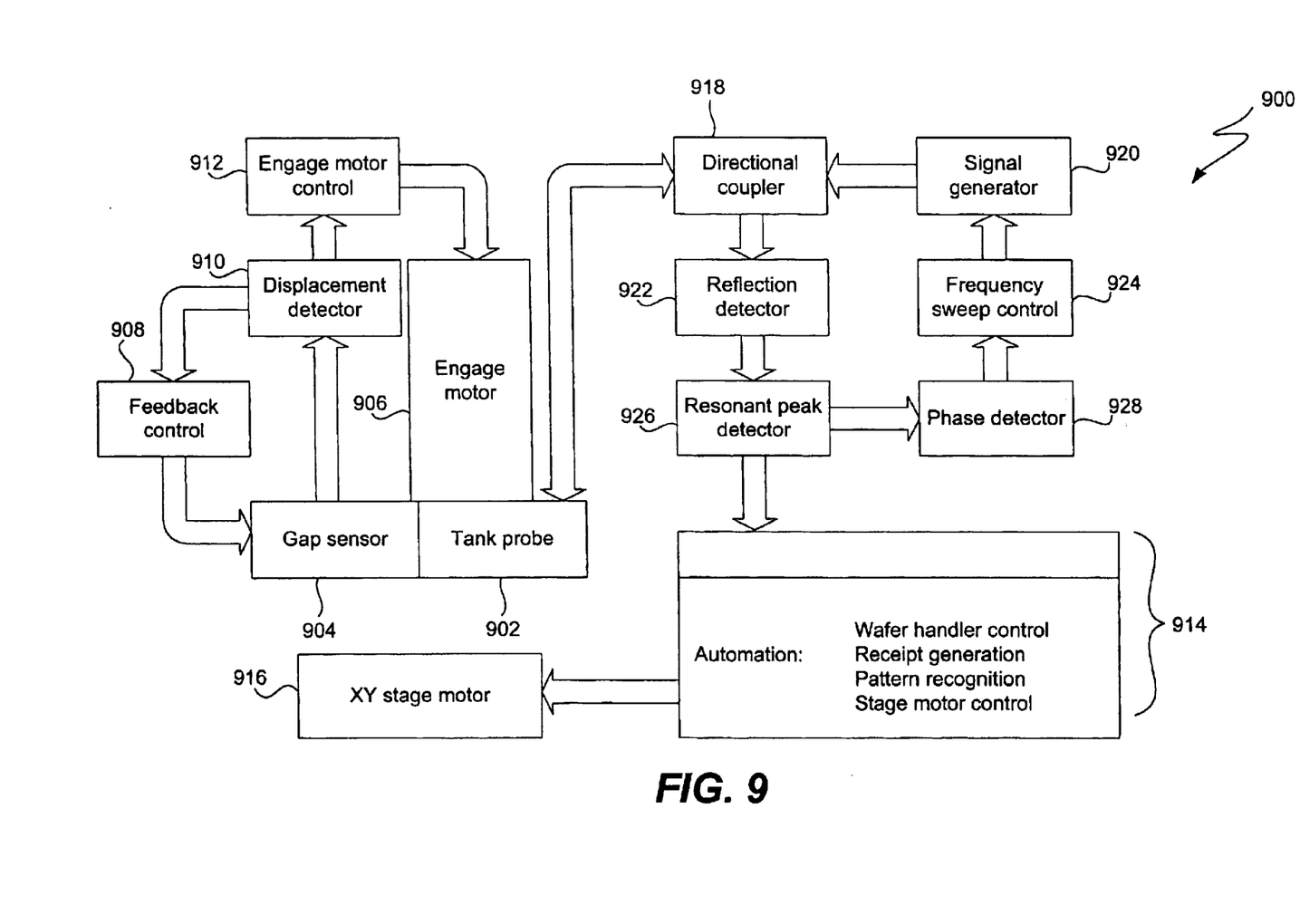
FIG. 9 illustrates a block diagram of a test system capable of utilizing a tank probe of the present invention.

FIG. 9 illustrates a block diagram of a test system 900 capable of utilizing a tank probe of the present invention, Test system 900 includes tank probe 902 that is connected to and positioned by the combination of a gap sensor 904 and an actuator or an engaging motor 906. Feedback control module 908 is connected to gap sensor 904 and receives information from displacement detector 910. Actuator or engage motor control module 912 receives information from displacement detector 910 and then outputs signals to actuator or engage motor 906 to control the position of tank probe 902.

Data and analysis module 914 receives information from tank probe 902 and controls the stage motor 916, which controls the positioning of the stage that secures the specimen film structure. Analysis module 914 performs additional operations such as wafer handler controlling, recipe generation, and pattern recognition. The following various modules between analysis module 914 and tank probe 902 process and generate signals for conductivity testing: a directional coupler 918, a signal generator 920, a reflection detector 922, a frequency sweep controller 924, a resonant peak detector 926, and a frequency phase detector 928.

While this invention has been described in terms of several preferred embodiments, there are alteration, permutations, and equivalents, which fall within the scope of this invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

We claim:

1. A tank probe system for determining the conductivity of a material specimen comprising:
 a tank probe including an inductor and a capacitor;
 a measurement instrument connected to the tank probe by a transmission line, the measurement instrument including
  a signal generator that sends a driving signal to the tank probe,
   wherein the driving signal causes the tank probe to operate in a frequency range of between approximately 200 MHz and 1 Giga-hertz; and
  a signal analysis module configured to detect and measure a reflected signal from the tank probe and the frequency of the reflected signal, wherein the conductivity of the material specimen is determined from the reflected signal and the frequency of the reflected signal.

2. A tank probe system as recited in claim 1 wherein the inductor and capacitor of the tank probe are arranged to have an impedance that is approximately equal to the impedance of the transmission line and the signal generator.

3. A tank probe system as recited in claim 1 wherein the driving signal causes the tank probe to resonate at its resonant frequency.

4. A tank probe system as recited in claim 1 wherein the driving signal causes the tank probe to have an electromagnetic field that has a penetration depth that is approximately equal to the thickness of the material specimen.

5. A tank probe system as recited in claim 1 wherein the tank probe system is used in combination with a proximity sensor such that the tank probe can be maintained at approximately a constant separation distance from the material specimen.

6. A tank probe system as recited in claim 1 when the tank probe system is used in combination with a semiconductor fabrication device.

7. A tank probe system as recited in claim 1 wherein the inductor is coated with an elastic insulating material, whereby the insulation material allows the tank probe to be placed in contact with the material specimen during measurement without causing damage to the material specimen.

8. A tank probe system as recited in claim 1 further comprising a rod-shaped electromagnetic field focusing element that is positioned at a center of the inductor and extends perpendicularly from a plane in which the inductor is formed.

9. A tank probe system as recited in claim 1 comprising a second tank probe and a second measurement instrument to detect and measure a second reflected signal and the frequency of the second reflected signal.

10. A tank probe system as recited in claim 1 wherein the inductor and the capacitor of the probe are integrated circuits within the substrate.

11. A tank probe system as recited in claim 10 wherein the inductor is a coil having an outer diameter of approximately 100 microns.

12. A tank probe system as recited in claim 10 wherein the inductor coil is formed of a ferrite material.

13. The tank probe system as recited in claim 1 wherein the tank probe has an impedance and wherein the tank probe can be tuned such that the reflected signal is minimized when the impedance matches an impedance of the signal generator and the transmission line.

14. A method for measuring the conductivity of a material specimen comprising:
 configuring tank probe, which includes an inductor and a capacitor, to have an impedance that is approximately equal to the impedance of a transmission line and a signal generator, the transmission line connecting the tank probe and the signal generator;
 setting the signal generator to send a driving signal to the tank probes that the tank probe is driving at resonant frequency,
  wherein the driving signal causes the tank probe to operate in a frequency range of between approximately 200 MHz and 1 Giga-hertz;
 detecting and measuring a signal that is reflected out of the tank probe; and
 detecting and measuring the frequency of the signal that is reflected, whereby the signal and frequency of the signal provide information that is sufficient to determine the conductivity of the material specimen.

15. A method for measuring the conductivity of a material specimen as recited in claim 14 further comprising:
 regulating the distance between the tank probe and the material specimen such that the distance is maintained at an average desired distance.

16. A to probe system for determining the conductivity of a material specimen comprising:
 a tank probe including em inductor and a capacitor, wherein the inductor and the capacitor are integrated circuits within a semiconductor substrate;
 a measurement instrument connected to the tank probe by a transmission line, the measurement instrument including
  a signal generator that sends a driving signal to the tank probe,
   wherein the driving signal causes the tank probe to operate in a frequency range of between approximately 200 MHz and 1 Giga-hertz; and
  a signal analysis module configured to detect and measure a reflected signal from the tank probe and the frequency of the reflected signal, wherein the conductivity of the material specimen is determined from the reflected signal and the frequency of the reflected signal.

17. A tank probe system as recited in claim 16 wherein the inductor and capacitor of the tank probe are arranged to have an impedance that is approximately equal to the impedance of the transmission line and the signal generator.

18. A tank probe system as recited in claim 16 wherein the driving signal causes the tank probe to resonate at its resonant frequency.

19. A tank probe system as recited in claim 16 wherein the inductor is coated with an elastic insulating material, whereby the insulating material allows the tank probe to be placed in contact with the specimen during measurement without causing damage to the material specimen.

20. A tank probe system as recited in claim 16 further comprising a rod-shaped electromagnetic field focusing element that is positioned at a center of the inductor and extends perpendicularly from a plane in which the inductor is formed.

21. A tank probe system as recited in claim 16 further comprising a second tank probe and a second measurement instrument configured to detect and measure a second reflected signal and the frequency of the second reflected signal.

22. The tank probe system as recited in claim 16 wherein the tank probe has an impedance, and wherein the tank probe can be tuned such that the reflected signal is minimized when the impedance matches an impedance of the signal generator and the transmission line.

* * * * *

UNITED STATES PATENT AND TRADEMARK OFFICE
CERTIFICATE OF CORRECTION

PATENT NO. : 6,794,886 B1
DATED : September 21, 2004
INVENTOR(S) : Chen et al.

It is certified that error appears in the above-identified patent and that said Letters Patent is hereby corrected as shown below:

Column 1,
Line 41, change "adjacent 30" to -- adjacent --.
Line 49, change "layers arc" to -- layers are --.

Column 2,
Line 34, change "and arc" to -- and are --.

Column 4,
Line 12, change "100 urn" to -- 100 um --.

Column 5,
Line 47, change "clement 210" to -- element 210 --.
Line 55, change "or Teflon" to -- or a fluoropolymer resin (such as Teflon, which is available from Dupont, Wilmington, DE) --.

Column 7,
Line 3, change "life curve" to -- lift curve --.

Column 9,
Line 36, change "claim 1 when" to -- claim 1 wherein --.
Line 40, change "insulation material" to -- insulating material --.
Line 48, change "comprising" to -- further comprising --.
Line 49, change "instrument to" to -- instrument configured to --.
Line 53, change "of the probe" to -- of the tank probe --.
Line 54, change "the substrate" to -- a semiconductor substrate --.
Line 66, change "configuring tank" to -- configuring a tank --.

UNITED STATES PATENT AND TRADEMARK OFFICE
CERTIFICATE OF CORRECTION

PATENT NO. : 6,794,886 B1
DATED : September 21, 2004
INVENTOR(S) : Chen et al.

It is certified that error appears in the above-identified patent and that said Letters Patent is hereby corrected as shown below:

Column 10,
Line 13, change "and frequency" to -- and the frequency --.
Line 21, change "A to probe" to -- A tank probe --.
Line 23, change "em inductor" to -- an inductor --.
Line 50, change "the specimen" to -- the material specimen --.

Signed and Sealed this

Fifteenth Day of February, 2005

JON W. DUDAS
*Director of the United States Patent and Trademark Office*